(12) United States Patent
Esbech et al.

(10) Patent No.: US 10,383,711 B2
(45) Date of Patent: Aug. 20, 2019

(54) FOCUS SCANNING APPARATUS RECORDING COLOR

(71) Applicant: 3SHAPE A/S, Copenhagen (DK)

(72) Inventors: Bo Esbech, Gentofte (DK); Christian Romer Rosberg, Bronshoj (DK); Mike Van Der Poel, Rodovre (DK); Rasmus Kjaer, Copenhagen (DK); Michael Vinther, Copenhagen (DK); Karl-Josef Hollenbeck, Copenhagen (DK)

(73) Assignee: 3SHAPE A/S, Copenhagen K (DK)

( * ) Notice: Subject to any disclaimer, the term of this patent is extended or adjusted under 35 U.S.C. 154(b) by 0 days.

(21) Appl. No.: 15/888,416

(22) Filed: Feb. 5, 2018

(65) Prior Publication Data

US 2018/0221117 A1     Aug. 9, 2018

Related U.S. Application Data

(63) Continuation of application No. 14/764,087, filed as application No. PCT/EP2014/052842 on Feb. 13, 2014, now Pat. No. 9,962,244.

(Continued)

(30) Foreign Application Priority Data

Feb. 13, 2013    (DK) .................................. 2013 70077

(51) Int. Cl.
*H01J 40/14*    (2006.01)
*A61C 9/00*    (2006.01)
(Continued)

(52) U.S. Cl.
CPC ............ *A61C 9/0073* (2013.01); *A61C 9/006* (2013.01); *A61C 9/0066* (2013.01); *G01B 11/24* (2013.01);
(Continued)

(58) Field of Classification Search
CPC . G01B 11/24; G01B 11/2509; G01B 11/2518; G01J 3/508
(Continued)

(56) References Cited

U.S. PATENT DOCUMENTS 6,097,854 A    8/2000  Szeliski et al.
6,750,873 B1   6/2004  Bernardini et al.
(Continued)

FOREIGN PATENT DOCUMENTS

CN    1363827 A     8/2002
CN    101667303 A   3/2010
(Continued)

OTHER PUBLICATIONS

Office Action (Notice of Reasons for Rejection) dated Jan. 9, 2018, by the Japanese Patent Office in Japanese Patent Application No. 2015-557430, and an English Translation of the Office Action. (8 pages).

(Continued)

*Primary Examiner* — Kevin K Pyo
(74) *Attorney, Agent, or Firm* — Buchanan Ingersoll & Rooney P.C.

(57) ABSTRACT

Disclosed are a scanner system and a method for recording surface geometry and surface color of an object where both surface geometry information and surface color information for a block of the image sensor pixels at least partly from one 2D image recorded by the color image sensor. A particular application is within dentistry, particularly for intraoral scanning.

51 Claims, 4 Drawing Sheets

Related U.S. Application Data

(60) Provisional application No. 61/764,178, filed on Feb. 13, 2013.

(51) Int. Cl.
  *G01B 11/25* (2006.01)
  *G01J 3/51* (2006.01)
  *G01J 3/02* (2006.01)
  *G01J 3/50* (2006.01)
  *G01B 11/24* (2006.01)

(52) U.S. Cl.
  CPC ...... *G01B 11/2509* (2013.01); *G01B 11/2513* (2013.01); *G01B 11/2518* (2013.01); *G01J 3/0208* (2013.01); *G01J 3/0224* (2013.01); *G01J 3/0237* (2013.01); *G01J 3/0278* (2013.01); *G01J 3/508* (2013.01); *G01J 3/51* (2013.01); *G01J 3/513* (2013.01)

(58) Field of Classification Search
  USPC .................................. 250/226, 234; 348/47
  See application file for complete search history.

(56) References Cited

U.S. PATENT DOCUMENTS

| | | | |
|---|---|---|---|
| 6,903,738 B2 * | 6/2005 | Pfister | G06T 15/205 345/420 |
| 7,106,348 B2 | 9/2006 | Matsumoto et al. | |
| 7,698,068 B2 | 4/2010 | Babayoff | |
| 8,102,538 B2 | 1/2012 | Babayoff | |
| 9,212,898 B2 | 12/2015 | Banyay | |
| 9,456,754 B2 | 10/2016 | Kocherscheidt | |
| 9,962,244 B2 * | 5/2018 | Esbech | G01J 3/513 |
| 2002/0122192 A1 | 9/2002 | Ott | |
| 2005/0285027 A1 | 12/2005 | Favalora et al. | |
| 2007/0035641 A1 | 2/2007 | Yamada et al. | |
| 2010/0067789 A1 | 3/2010 | Cai et al. | |
| 2010/0145898 A1 | 6/2010 | Malfliet et al. | |
| 2011/0080576 A1 | 4/2011 | Thiel et al. | |
| 2011/0134225 A1 | 6/2011 | Saint-Pierre et al. | |
| 2011/0221880 A1 | 9/2011 | Liang et al. | |
| 2012/0062716 A1 | 3/2012 | Dillon et al. | |
| 2012/0075425 A1 | 3/2012 | Thiel | |
| 2012/0092461 A1 | 4/2012 | Fisker et al. | |
| 2012/0140243 A1 | 6/2012 | Colonna de Lega | |
| 2013/0070128 A1 | 3/2013 | Suzuki et al. | |
| 2013/0101176 A1 | 4/2013 | Park et al. | |
| 2013/0236850 A1 | 9/2013 | Wu et al. | |
| 2014/0022356 A1 | 1/2014 | Fisker et al. | |
| 2014/0146142 A1 | 5/2014 | Duret et al. | |
| 2015/0015701 A1 | 1/2015 | Yu | |
| 2015/0029367 A1 | 1/2015 | Tanaka | |
| 2018/0270474 A1 | 9/2018 | Liu | |

FOREIGN PATENT DOCUMENTS

| | | |
|---|---|---|
| CN | 102008282 A | 4/2011 |
| CN | 102112845 A | 6/2011 |
| CN | 102402799 A | 4/2012 |
| CN | 102802520 A | 11/2012 |
| EP | 2 241 248 A2 | 10/2010 |
| JP | 2004-029373 A | 1/2004 |
| JP | 20017117152 A | 5/2007 |
| JP | 2009109263 A | 5/2009 |
| WO | WO 2010/145669 A1 | 12/2010 |
| WO | WO 2012/007003 A1 | 1/2012 |
| WO | WO 2012/083967 A1 | 6/2012 |
| WO | WO 2013/008097 A1 | 1/2013 |
| WO | 2015/015289 A2 | 2/2015 |

OTHER PUBLICATIONS

International Search Report (PCT/ISA/210) dated Jul. 7, 2014, by the European Patent Office as the International Searching Authority for International Application No. PCT/EP2014/052842.

The First Office Action dated Aug. 2, 2016, by the State Intellectual Property Office of People's Republic of China in corresponding Chinese Patent Application No. 201480020976.3, and an English Translation of the Office Action. (18 pages).

The First Chinese Search dated Jul. 25, 2016, by the State Intellectual Property Office of People's Republic of China in corresponding Chinese Patent Application No. 201480020976.3. (2 pages).

Office Action (Communication pursuant to Article 94(3) EPC) dated Jul. 13, 2018, by the European Patent Office in corresponding European Application No. 14 704 165.1-1022. (10 pages).

"Bayer filter" Wikipedia, Jul. 4, 2018, XP-055490506, 4 pages.

Align Technology, Inc. Petitioner V., 3SHAPE A/S, Patent Owner, Petition for Inter Partes Review of U.S. Pat. No. 9,962,244, Case No. IPR2019-00118, U.S. Pat. No. 9,962,244, filed Nov. 5, 2018, 93 pages.

Align Technology, Inc. Petitioner V., 3SHAPE A/S, Patent Owner, Petition for Inter Partes Review of U.S. Pat. No. 9,962,244, Case No. IPR2019-00117, U.S. Pat. No. 9,962,244, filed Nov. 5, 2018, 98 pages.

Align Technology, Inc. Petitioner V., 3SHAPE A/S Patent Owner, Petition for Post-Grant Review of U.S. Pat. No. 9,962,244, Case No. PGR2018-00103, U.S. Pat. No. 9,962,244, filed Oct. 30, 2018, 119 pages.

Align Technology, Inc. Petitioner V., 3SHAPE A/S, Patent Owner, Petition for Post-Grant Review of U.S. Pat. No. 9,962,244, Case No. PGR2018-00104, U.S. Pat. No. 9,962,244, filed Oct. 26, 2018, 107 pages.

Exhibit 1002 in PGR2018-00103—Prosecution File History for the '244 patent ("244 patent file history"), filed Oct. 30, 2018, 1039 pages.

Align Technology, Inc. Petitioner, Declaration of Dr. Chandrajit L. Bajaj, Ph.D. In Support of Inter Partes Review of U.S. Pat. No. 9,962,244, Case Nos. IPR2019-00117 U.S. Pat. No. 9,962,244, 3SHAPE A/S Patent Owner, filed Nov. 5, 2018, 316 pages.

Exhibit 1004 in PGR2018-00103—Curriculum vitae of Dr. Chandra Bajaj, Ph.D., filed Oct. 30, 2018, 316 pages.

Agini, Andreas, et al. Digital Dental Revolution: The Learning Curve. Quintessence Publishing, First edition, 2015.

Karatas et al., "Three-dimensional imaging techniques: A literature review," European Journal of Dentistry, vol. 8, Issue 1, 2014, pp. 132-140.

Broadbent, B.H., "A New X-Ray Technique and Its Application to Orthodontia," The Angle Orthodontist, vol. 1, No. 2, 1931, pp. 45-66.

Hajeer et al., Current Products and Practices Applications of 3D imaging in orthodontics: Part II, Journal of Orthodontics, vol. 31, (2004), pp. 154-162.

Yamany et al., "Free-Form Surface Registration Using Surface Signatures," The Proceedings of the Seventh IEEE International Conference on Computer Vision, Sep. 20-27, 1999, 7 pages.

Ireland et al., "3D surface imaging in dentistry—what we are looking at," British Dental Journal, vol. 205, No. 7, Oct. 11, 2008, pp. 387-392.

Remondino et al., Image-Based 3D Modelling: A Review, The Photogrammetric Record, vol. 21, No. 115, Sep. 2006, pp. 269-291.

Ting-Shu et al., "Intraoral Digital Impression Technique: A Review," J. Prosthodontics, vol. 24, No. 4, pp. 313-321.

Zimmerman et al., "Intraoral scanning systems—A current overview," Int. J. Comput. Dent., vol. 18, No. 2, 2015, pp. 101-129.

Imburgia et al., "Accuracy of four intraoral scanners in oral implantology: a comparative in vitro study," BMC Oral Health, vol. 17, No. 1, 2017, p. 17-92.

Park et al., "Changes in views on digital intraoral scanners among dental hygienists after training in digital impression taking," BMC Oral Health, vol. 15, No. 1, 2015, p. 151 ("Park Article").

Logozzo et al., "Recent advances in dental optics—Part I: 3D intraoral scanners for restorative dentistry," Optics and Lasers in Engineering, vol. 54, 2014, pp. 203-221.

U.S. Appl. No. 61/764,178 to Esbech et al. Feb. 13, 2013 ("The Provisional Application").

(56) References Cited

OTHER PUBLICATIONS

Align Technology, Inc. Petitioner, Corrected Petition for Post-Grant Review of U.S. Pat. No. 9,962,244, Case No. PGR2018-00103 U.S. Pat. No. 9,962,244, 3SHAPE A/S Patent Owner, filed Oct. 30, 2018, 119 pages.

Align Technology, Inc. Petitioner, Declaration of Dr. Chandrajit L Bajaj, PH.D. In Support of Post-Grant Review of U.S. Pat. No. 9,962,244, Case Nos. PGR2018-00103 U.S. Pat. No. 9,962,244, 3SHAPE A/S Patent Owner, filed Oct. 30, 2018, 318 pages.

Align Technology, Inc. Petitioner, Second Corrected Declaration of Dr. Chandrajit L. Bajaj, Ph.D. In Support of Post-Grant Review of U.S. Pat. No. 9,962,244, Case No. PGR2018-00103 U.S. Pat. No. 9,962,244, 3SHAPE A/S Patent Owner, filed Oct. 30, 2018, 318 pages.

Align Technology, Inc. Petitioner, Second Corrected Petition for Post-Grant Review of U.S. Pat. No. 9,962,244, Case No. PGR2018-00103 U.S. Pat. No. 9,962,244, 3SHAPE A/S Patent Owner, filed Oct. 30, 2018, 119 pages.

Corrected Declaration of Dr. Chandrajit L. Bajaj, Ph.D. In Support of Post-Grant Review of U.S. Pat. No. 9,962,244, Align Technology, Inc. Petitioner, Case Nos. PGR2018-00103 U.S. Pat. No. 9,962,244, 3SHAPE A/S Patent Owner, filed Oct. 30, 2018, 318 pages.

Chandrajit L. Bajaj, CV_Case_ History, Align Ex. 1004 U.S. Pat. No. 9,962,244, filed Oct. 30, 2018, 39 pages.

Align Technology, Inc. Petitioner, Declaration of Dr. Chandrajit L. Bajaj, Ph.D. In Support of Post-Grant Review of U.S. Pat. No. 9,962,244, Case Nos. PGR2018-00104 U.S. Pat. No. 9,962,244, 3SHAPE A/S Patent Owner, filed Oct. 26, 2018, 318 pages.

Align Technology, Inc. Petitioner, Declaration of Dr. Chandrajit L. Bajaj, Ph.D. In Support of Inter Partes Review of U.S. Pat. No. 9,962,244, Case Nos. IPR2019-00118 U.S. Pat. No. 9,962,244, 3SHAPE A/S Patent Owner, filed Nov. 5, 2018, 316 pages.

*Align Technology, Inc.* Petitioner V., *3Shape A/S*, Patent Owner, Patent Owner's Preliminary Response to the Petition for Post-Grant Review of U.S. Pat. No. 9,962,244, Case No. PGR2018-00104, U.S. Pat. No. 9,962,244, filed Feb. 19, 2019, 64 pages.

*Align Technology, Inc.* Petitioner V., *3Shape A/S*, Patent Owner, Patent Owner's Preliminary Response to the Petition for Inter Partes Review of U.S. Pat. No. 9,962,244, Case No. IPR2019-00117, U.S. Pat. No. 9,962,244, filed Mar. 4, 2019, 63 pages.

*Align Technology, Inc.* Petitioner V., *3Shape A/S*, Patent Owner, Patent Owner's Preliminary Response to the Petition for Post-Grant Review of U.S. Pat. No. 9,962,244, Case No. PGR2018-00103, U.S. Pat. No. 9,962,244, filed Feb. 19, 2019, 64 pages.

*Align Technology, Inc.* Petitioner V., *3Shape A/S*, Patent Owner, Patent Owner's Preliminary Response to the Petition for Inter Partes Review of U.S. Pat. No. 9,962,244, Case No. IPR2019-00118, U.S. Pat. No. 9,962,244, filed Mar. 4, 2019, 62 pages.

Callieri et al., "Reconstructing textured meshes from multiple range+rgb maps," Vision, Modeling, and Visualization, (Nov. 2002). (8 pages).

Horn et al., "Calculating the Reflectance Map," Applied Optics, (Jun. 1979), vol. 18, No. 11, pp. 1770-1779.

Montes et al., "An Overview of BRDF Models," University of Granada. (26 pages).

Sato, Yoichi, "Object Shape and Reflectance Modeling from Color Image Sequence," The Robotics Institute: Carnegie Mellon University, (Jan. 1997). (158 pages).

Office Action (First Office Action) dated Apr. 30, 2019, by the State Intellectual Property Office (SIPO) of the People's Republic of China in corresponding Chinese Patent Application No. 201710806147.3 and an English Translation of the Office Action. (10 pages).

* cited by examiner

FOCUS SCANNING APPARATUS RECORDING COLOR

CROSS REFERENCE TO RELATED APPLICATIONS

The present application is a continuation of U.S. application Ser. No. 14/764,087, filed on Jul. 28, 2015, which is a U.S. National Stage of International Application No. PCT/EP2014/052842, filed on Feb. 13, 2014, which claims the benefit of U.S. Provisional Application No. 61/764,178, filed on Feb. 13, 2013, and the benefit of Danish Application No. PA 2013-70077, filed on Feb. 13, 2013. The entire contents of each of U.S. application Ser. No. 14/764,087, International Application No. PCT/EP2014/052842, U.S. Provisional Application No. 61/764,178, and Danish Application No. PA 2013-70077 are hereby incorporated herein by reference in their entirety.

FIELD OF THE APPLICATION

The application relates to three dimensional (3D) scanning of the surface geometry and surface color of objects. A particular application is within dentistry, particularly for intraoral scanning.

BACKGROUND 3D scanners are widely known from the art, and so are intraoral dental 3D scanners (e.g., Sirona Cerec, Cadent Itero, 3Shape TRIOS).

The ability to record surface color is useful in many applications. For example in dentistry, the user can differentiate types of tissue or detect existing restorations. For example in materials inspection, the user can detect surface abnormalities such as crystallization defects or discoloring. None of the above is generally possible from surface geometry information alone.

WO2010145669 mentions the possibility of recording color. In particular, several sequential images, each taken for an illumination in a different color—typically blue, green, and red—are combined to form a synthetic color image. This approach hence requires means to change light source color, such as color filters. Furthermore, in handheld use, the scanner will move relative to the scanned object during the illumination sequence, reducing the quality of the synthetic color image.

Also U.S. Pat. No. 7,698,068 and U.S. Pat. No. 8,102,538 (Cadent Inc.) describe an intraoral scanner that records both geometry data and texture data with one or more image sensor(s). However, there is a slight delay between the color and the geometry recording, respectively. U.S. Pat. No. 7,698,068 requires sequential illumination in different colors to form a synthetic image, while U.S. Pat. No. 8,102,538 mentions white light as a possibility, however from a second illumination source or recorded by a second image sensor, the first set being used for recording the geometry.

WO2012083967 discloses a scanner for recording geometry data and texture data with two separate cameras. While the first camera has a relatively shallow depth of field as to provide focus scanning based on multiple images, the second camera has a relatively large depth of field as to provide color texture information from a single image.

Color-recording scanning confocal microscopes are also known from the prior art (e.g., Keyence VK9700; see also JP2004029373). A white light illumination system along with a color image sensor is used for recording 2D texture, while a laser beam forms a dot that is scanned, i.e., moved over the surface and recorded by a photomultiplier, providing the geometry data from many depth measurements, one for each position of the dot. The principle of a moving dot requires the measured object not to move relative to the microscope during measurement, and hence is not suitable for handheld use.

SUMMARY

One aspect of this application is to provide a scanner system and a method for recording surface geometry and surface color of an object, and where surface geometry and surface color are derived from the same captured 2D images.

One aspect of this application is to provide a scanner system for recording surface geometry and surface color of an object, and wherein all 2D images are captured using the same color image sensor.

One aspect of this application is to provide a scanner system and a method for recording surface geometry and surface color of an object, in which the information relating to the surface geometry and to the surface color are acquired simultaneously such that an alignment of data relating to the recorded surface geometry and data relating to the recorded surface color is not required in order to generate a digital 3D representation of the object expressing both color and geometry of the object.

Disclosed is a scanner system for recording surface geometry and surface color of an object, the scanner system comprising:
  a multichromatic light source configured for providing a multichromatic probe light for illumination of the object,
  a color image sensor comprising an array of image sensor pixels for capturing one or more 2D images of light received from said object, and
  a data processing system configured for deriving both surface geometry information and surface color information for a block of said image sensor pixels at least partly from one 2D image recorded by said color image sensor.

Disclosed is a method of recording surface geometry and surface color of an object, the method comprising:
  obtaining a scanner system comprising a multichromatic light source and a color image sensor comprising an array of image sensor pixels;
  illuminating the surface of said object with multichromatic probe light from said multichromatic light source;
  capturing a series of 2D images of said object using said color image sensor; and
  deriving both surface geometry information and surface color information for a block of said image sensor pixels at least partly from one captured 2D image.

In the context of the present application, the phrase "surface color" may refer to the apparent color of an object surface and thus in some cases, such as for semi-transparent or semi-translucent objects such as teeth, be caused by light from the object surface and/or the material below the object surface, such as material immediately below the object surface.

In the context of the present application, the phrase "derived at least partly from one 2D image" refers to the situation where the surface geometry information for a given block of image sensor pixels at least in part is derived from one 2D image and where the corresponding surface color information at least in part is derived from the same 2D image. The phase also covers cases where the surface geometry information for a given block of image sensor pixels at least in part is derived from a plurality of 2D images of a series of captured 2D images and where the corresponding surface color information at least in part is derived from the same 2D images of that series of captured 2D images.

An advantage of deriving both surface geometry information and surface color information for a block of said image sensor pixels at least partly from one 2D image is that a scanner system having only one image sensor can be realized.

It is an advantage that the surface geometry information and the surface color information are derived at least partly from one 2D image, since this inherently provides that the two types of information are acquired simultaneously. There is hence no requirement for an exact timing of the operation of two color image sensors, which may the case when one image sensor is used for the geometry recording and another for color recording. Equally there is no need for an elaborate calculation accounting for significant differences in the timing of capturing of 2D images from which the surface geometry information is derived and the timing of the capturing of 2D images from which the surface color information is derived.

The present application discloses is a significant improvement over the state of the art in that only a single image sensor and a single multichromatic light source is required, and that surface color and surface geometry for at least a part of the object can be derived from the same 2D image or 2D images, which also means that alignment of color and surface geometry is inherently perfect. In the scanner system according to the present application, there is no need for taking into account or compensating for relative motion of the object and scanner system between obtaining surface geometry and surface color.

Since the surface geometry and the surface color are obtained at precisely the same time, the scanner system automatically maintains its spatial disposition with respect to the object surface while obtaining the surface geometry and the surface color. This makes the scanner system of the present application suitable for handheld use, for example as an intraoral scanner, or for scanning moving objects.

In some embodiments, the data processing system is configured for deriving surface geometry information and surface color information for said block of image sensor pixels from a series of 2D images, such as from a plurality of the 2D images in a series of captured 2D images. I.e. the data processing system is capable of analyzing a plurality of the 2D images in a series of captured 2D images in order to derive the surface geometry information for a block of image sensor pixels and to also derive surface color information from at least one of the 2D images from which the surface geometry information is derived.

In some embodiments, the data processing system is configured for deriving surface color information from a plurality of 2D images of a series of captured 2D images and for deriving surface geometry information from at least one of the 2D images from which the surface color information is derived.

In some embodiments, the data processing system is configured for deriving surface geometry information from a plurality of 2D images of a series of captured 2D images and for deriving surface color information from at least one of the 2D images from which the surface geometry information is derived.

In some embodiments, the set of 2D images from which surface color information is derived from is identical to the set of 2D images from which surface geometry information is derived from.

In some embodiments, the data processing system is configured for generating a sub-scan of a part of the object surface based on surface geometry information and surface color information derived from a plurality of blocks of image sensor pixels. The sub-scan expresses at least the geometry of the part of the object and typically one sub-scan is derived from one stack of captured 2D images.

In some embodiments, all 2D images of a captured series of images are analyzed to derive the surface geometry information for each block of image sensor pixels on the color image sensor.

For a given block of image sensor pixels the corresponding portions of the captured 2D images in the stack may be analyzed to derive the surface geometry information and surface color information for that block.

In some embodiments, the surface geometry information relates to where the object surface is located relative to the scanner system coordinate system for that particular block of image sensor pixels.

One advantage of the scanner system and the method of the current application is that the informations used for generating the sub-scan expressing both geometry and color of the object (as seen from one view) are obtained concurrently.

Sub-scans can be generated for a number of different views of the object such that they together cover the part of the surface.

In some embodiments, the data processing system is configured for combining a number of sub-scans to generate a digital 3D representation of the object. The digital 3D representation of the object then preferably expresses both the recorded geometry and color of the object.

The digital 3D representation of the object can be in the form of a data file. When the object is a patient's set of teeth the digital 3D representation of this set of teeth can e.g. be used for CAD/CAM manufacture of a physical model of the patient's set teeth.

The surface geometry and the surface color are both determined from light recorded by the color image sensor.

In some embodiments, the light received from the object originates from the multichromatic light source, i.e. it is probe light reflected or scattered from the surface of the object.

In some embodiments, the light received form the object comprises fluorescence excited by the probe light from the multichromatic light source, i.e. fluorescence emitted by fluorescent materials in the object surface.

In some embodiments, a second light source is used for the excitation of fluorescence while the multichromatic light source provides the light for obtaining the geometry and color of the object.

The scanner system preferably comprises an optical system configured for guiding light emitted by the multichromatic light source towards the object to be scanned and for guiding light received from the object to the color image sensor such that the 2D images of said object can be captured by said color image sensor.

In some embodiments, the scanner system comprises a first optical system, such as an arrangement of lenses, for transmitting the probe light from the multichromatic light source towards an object and a second optical system for imaging light received from the object at the color image sensor.

In some embodiments, single optical system images the probe light onto the object and images the object, or at least a part of the object, onto the color image sensor, preferably along the same optical axis, however in opposite directions along optical axis. The scanner may comprise at least one beam splitter located in the optical path, where the beam splitter is arranged such that it directs the probe light from the multichromatic light source towards the object while it directs light received from the object towards the color image sensor.

Several scanning principles are suitable, such as triangulation and focus scanning.

In some embodiments, the scanner system is a focus scanner system operating by translating a focus plane along an optical axis of the scanner system and capturing the 2D images at different focus plane positions such that each series of captured 2D images forms a stack of 2D images. The focus plane position is preferably shifted along an optical axis of the scanner system, such that 2D images captured at a number of focus plane positions along the optical axis forms said stack of 2D images for a given view of the object, i.e. for a given arrangement of the scanner system relative to the object. After changing the arrangement of the scanner system relative to the object a new stack of 2D images for that view can be captured. The focus plane position may be varied by means of at least one focus element, e.g., a moving focus lens.

In some focus scanner embodiments, the scanner system comprises a pattern generating element configured for incorporating a spatial pattern in said probe light.

In some embodiments, the pattern generating element is configured to provide that the probe light projected by scanner system onto the object comprises a pattern consisting of dark sections and sections with light having the a wavelength distribution according to the wavelength distribution of the multichromatic light source.

In some embodiments, the multichromatic light source comprises a broadband light source, such as a white light source In some embodiments, the pixels of the color image sensor and the pattern generating element are configured to provide that each pixel corresponds to a single bright or dark region of the spatial pattern incorporated in said probe light.

For a focus scanner system the surface geometry information for a given block of image sensor pixels is derived by identifying at which distance from the scanner system the object surface is in focus for that block of image sensor pixels.

In some embodiments, deriving the surface geometry information and surface color information comprises calculating for several 2D images, such as for several 2D images in a captured stack of 2D images, a correlation measure between the portion of the 2D image captured by said block of image sensor pixels and a weight function. Here the weight function is preferably determined based on information of the configuration of the spatial pattern. The correlation measure may be calculated for each 2D image of the stack.

The scanner system may comprise means for evaluating a correlation measure at each focus plane position between at least one image pixel and a weight function, where the weight function is determined based on information of the configuration of the spatial pattern.

In some embodiments, deriving the surface geometry information and the surface color information for a block of image sensor pixels comprises identifying the position along the optical axis at which the corresponding correlation measure has a maximum value. The position along the optical axis at which the corresponding correlation measure has a maximum value may coincide with the position where a 2D image has been captured but it may even more likely be in between two neighboring 2D images of the stack of 2D images.

Determining the surface geometry information may then relate to calculating a correlation measure of the spatially structured light signal provided by the pattern with the variation of the pattern itself (which we term reference) for every location of the focus plane and finding the location of an extremum of this stack of 2D images. In some embodiments, the pattern is static. Such a static pattern can for example be realized as a chrome-on-glass pattern.

One way to define the correlation measure mathematically with a discrete set of measurements is as a dot product computed from a signal vector, I=(I1, . . . , In), with n>1 elements representing sensor signals and a reference vector, f=(f1, . . . , fn), of reference weights. The correlation measure A is then given by $$A = f \cdot I = \sum_{i=1}^{n} f_i I_i$$

The indices on the elements in the signal vector represent sensor signals that are recorded at different pixels, typically in a block of pixels. The reference vector f can be obtained in a calibration step.

By using knowledge of the optical system used in the scanner, it is possible to transform the location of an extremum of the correlation measure, i.e., the focus plane into depth data information, on a pixel block basis. All pixel blocks combined thus provide an array of depth data. In other words, depth is along an optical path that is known from the optical design and/or found from calibration, and each block of pixels on the image sensor represents the end point of an optical path. Therefore, depth along an optical path, for a bundle of paths, yields a surface geometry within the field of view of the scanner, i.e. a sub-scan for the present view.

It can be advantageous to smooth and interpolate the series of correlation measure values, such as to obtain a more robust and accurate determination of the location of the maximum.

In some embodiments, the generating a sub-scan comprises determining a correlation measure function describing the variation of the correlation measure along the optical axis for each block of image sensor pixels and identifying for the position along the optical axis at which the correlation measure functions have their maximum value for the block.

In some embodiments, the maximum correlation measure value is the highest calculated correlation measure value for the block of image sensor pixels and/or the highest maximum value of the correlation measure function for the block of image sensor pixels.

For example, a polynomial can be fitted to the values of A for a pixel block over several images on both sides of the recorded maximum, and a location of a deducted maximum can be found from the maximum of the fitted polynomial, which can be in between two images. The deducted maximum is subsequently used as depth data information when deriving the surface geometry from the present view, i.e. when deriving a sub-scan for the view.

In some embodiments, the data processing system is configured for determining a color for a point on a generated sub-scan based on the surface color information of the 2D image of the series in which the correlation measure has its maximum value for the corresponding block of image sensor pixels. The color may e.g. be read as the RGB values for pixels in said block of image sensor pixels.

In some embodiments, the data processing system is configured for deriving the color for a point on a generated sub-scan based on the surface color informations of the 2D images in the series in which the correlation measure has its maximum value for the corresponding block of image sensor pixels and on at least one additional 2D image, such as a neighboring 2D image from the series of captured 2D images. The surface color information is still derived from at least one of the 2D images from which the surface geometry information is derived.

In some embodiments, the data processing system is configured for interpolating surface color information of at least two 2D images in a series when determining the sub-scan color, such as an interpolation of surface color information of neighboring 2D images in a series.

In some embodiments, the data processing system is configured for computing a smoothed color for a number of points of the sub-scan, where the computing comprises an averaging of sub-scan colors of different points, such as a weighted averaging of the colors of the surrounding points on the sub-scan.

Surface color information for a block of image sensor pixels is at least partially derived from the same image from which surface geometry information is derived. In case the location of the maximum of A is represented by a 2D image, then also color is derived from that same image. In case the location of the maximum of A is found by interpolation to be between two images, then at least one of those two images should be used to derive color, or both images using interpolation for color also. It is also possible to average color data from more than two images used in the determination of the location of the maximum of the correlation measure, or to average color from a subset or superset of multiple images used to derive surface geometry. In any case, some image sensor pixels readings are used to derive both surface color and surface geometry for at least a part of the scanned object.

Typically, there are three color filters, so the overall color is composed of three contributions, such as red, green, and blue, or cyan, magenta, and yellow. Note that color filters typically allow a range of wavelengths to pass, and there is typically cross-talk between filters, such that, for example, some green light will contribute to the intensity measured in pixels with red filters.

For an image sensor with a color filter array, a color component $c_j$ within a pixel block can be obtained as $$c_j = \sum_{i=1}^{n} g_{j,i} I_i$$

where $g_{j,i}=1$ if pixel i has a filter for color $c_j$, 0 otherwise. For an RGB filter array like in a Bayer pattern, j is one of red, green, or blue. Further weighting of the individual color components, i.e., color calibration, may be required to obtain natural color data, typically as compensation for varying filter efficiency, illumination source efficiency, and different fraction of color components in the filter pattern. The calibration may also depend on focus plane location and/or position within the field of view, as the mixing of the light source component colors may vary with those factors.

In some embodiments, surface color information is obtained for every pixel in a pixel block. In color image sensors with a color filter array or with other means to separate colors such as diffractive means, depending on the color measured with a particular pixel, an intensity value for that color is obtained. In other words, in this case a particular pixel has a color value only for one color. Recently developed color image sensors allow measurement of several colors in the same pixel, at different depths in the substrate, so in that case, a particular pixel can yield intensity values for several colors. In summary, it is possible to obtain a resolution of the surface color data that is inherently higher than that of the surface geometry information.

In the embodiments where the resolution of the derived color is higher than the resolution of the surface geometry for the generated digital 3D representation of the object, a pattern will be visible when at least approximately in focus, which preferably is the case when color is derived. The image can be filtered such as to visually remove the pattern, however at a loss of resolution. In fact, it can be advantageous to be able to see the pattern for the user. For example in intraoral scanning, it may be important to detect the position of a margin line, the rim or edge of a preparation. The image of the pattern overlaid on the geometry of this edge is sharper on a side that is seen approximately perpendicular, and more blurred on the side that is seen at an acute angle. Thus, a user, who in this example typically is a dentist or dental technician, can use the difference in sharpness to more precisely locate the position of the margin line than may be possible from examining the surface geometry alone.

High spatial contrast of an in-focus pattern image on the object is desirable to obtain a good signal to noise ratio of the correlation measure on the color image sensor. Improved spatial contrast can be achieved by preferential imaging of the specular surface reflection from the object on the color image sensor. Thus, some embodiments comprise means for preferential/selective imaging of specularly reflected light. This may be provided if the scanner further comprises means for polarizing the probe light, for example by means of at least one polarizing beam splitter.

In some embodiments, the polarizing optics is coated such as to optimize preservation of the circular polarization of a part of the spectrum of the multichromatic light source that is used for recording the surface geometry.

The scanner system may further comprise means for changing the polarization state of the probe light and/or the light received from the object. This can be provided by means of a retardation plate, preferably located in the optical path. In some embodiments, the retardation plate is a quarter wave retardation plate.

Especially for intraoral applications where the scanned object e.g. is the patient's set or teeth, the scanner can have an elongated tip, with means for directing the probe light and/or imaging an object. This may be provided by means of at least one folding element. The folding element could be a light reflecting element such as a mirror or a prism. The probe light then emerges from the scanner system along an optical axis at least partly defined by the folding element.

For a more in-depth description of the focus scanning technology, see WO2010145669.

In some embodiments, the data processing system is configured for determining the color of a least one point of the generated digital 3D representation of the object, such that the digital 3D representation expresses both geometry and color profile of the object. Color may be determined for several points of the generated digital 3D representation such that the color profile of the scanned part of the object is expressed by the digital 3D representation.

In some embodiments determining the object color comprises computing a weighted average of color values derived for corresponding points in overlapping sub-scans at that point of the object surface. This weighted average can then be used as the color of the point in the digital 3D representation of the object.

In some embodiments the data processing system is configured for detecting saturated pixels in the captured 2D images and for mitigating or removing the error in the derived surface color information or the sub-scan color caused by the pixel saturation.

In some embodiments the error caused by the saturated pixel is mitigated or removed by assigning a low weight to the surface color information of the saturated pixel in the computing of the smoothed color of a sub-scan and/or by assigning a low weight to the color of a sub-scan computed based on the saturated pixel.

In some embodiments, the data processing system is configured for comparing the derived surface color information of sections of the captured 2D images and/or of the generated sub-scans of the object with predetermined color ranges for teeth and for oral tissue, and for suppressing the red component of the derived surface color information or sub-scan color for sections where the color is not in one of the two predetermined color ranges.

The scanner system disclosed here comprises a multichromatic light source, for example a white light source, for example a multi-die LED.

Light received from the scanned object, such as probe light returned from the object surface or fluorescence generated by the probe light by exciting fluorescent parts of the object, is recorded by the color image sensor. In some embodiments, the color image sensor comprises a color filter array such that every pixel in the color image sensor is a color-specific filter. The color filters are preferably arranged in a regular pattern, for example where the color filters are arranged according to a Bayer color filter pattern. The image data thus obtained are used to derive both surface geometry and surface color for each block of pixels. For a focus scanner utilizing a correlation measure, the surface geometry may be found from an extremum of the correlation measure as described above. In some embodiments, the surface geometry is derived from light in a first part of the spectrum of the probe light provided by the multichromatic light source.

Preferably, the color filters are aligned with the image sensor pixels, preferably such that each pixel has a color filter for a particular color only.

In some embodiments, the color filter array is such that its proportion of pixels with color filters that match the first part of the spectrum is larger than 50%.

In some embodiments, the surface geometry information is derived from light in a selected wavelength range of the spectrum provided by the multichromatic light source. The light in the other wavelength ranges is hence not used to derive the surface geometry information. This provides the advantage that chromatic dispersion of optical elements in the optical system of the scanner system does not influence the scanning of the object.

It can be preferable to compute the surface geometry only from pixels with one or two types of color filters. A single color requires no achromatic optics and is thus provides for a scanner that is easier and cheaper to build. Furthermore, folding elements can generally not preserve the polarization state for all colors equally well. When only some color(s) is/are used to compute surface geometry, the reference vector f will contain zeros for the pixels with filters for the other color(s). Accordingly, the total signal strength is generally reduced, but for large enough blocks of pixels, it is generally still sufficient. Preferentially, the pixel color filters are adapted for little cross-talk from one color to the other(s). Note that even in the embodiments computing geometry from only a subset of pixels, color is preferably still computed from all pixels.

In some embodiments, the color image sensor comprises a color filter array comprising at least three types of colors filters, each allowing light in a known wavelength range, W1, W2, and W3 respectively, to propagate through the color filter.

In some embodiments, the color filter array is such that its proportion of pixels with color filters that match the selected wavelength range of the spectrum is larger than 50%, such a wherein the proportion equals 32/36, 60/64 or 96/100.

In some embodiments, the selected wavelength range matches the W2 wavelength range.

In some embodiments, the color filter array comprises a plurality of cells of 6×6 color filters, where the color filters in positions (2,2) and (5,5) of each cell are of the W1 type, the color filters in positions (2,5) and (5,2) are of the W3 type. Here a W1 type of filter is a color tilter that allows light in the known wavelength range W1 to propagate through the color filter, and similar for W2 and W3 type of filters. In some embodiments, the remaining 32 color filters in the 6×6 cell are of the W2 type.

In a RGB color system, W1 may correspond to red light, W2 to green light, and W3 to blue light.

In some embodiments, the scanner is configured to derive the surface color with a higher resolution than the surface geometry.

In some embodiments, the higher surface color resolution is achieved by demosaicing, where color values for pixel blocks may be demosaiced to achieve an apparently higher resolution of the color image than is present in the surface geometry. The demosaicing may operate on pixel blocks or individual pixels.

In case a multi-die LED or another illumination source comprising physically or optically separated light emitters is used, it is preferable to aim at a Köhler type illumination in the scanner, i.e. the illumination source is defocused at the object plane in order to achieve uniform illumination and good color mixing for the entire field of view. In case color mixing is not perfect and varies with focal plane location, color calibration of the scanner will be advantageous.

In some embodiments, the pattern generating element is configured to provide that the spatial pattern comprises alternating dark and bright regions arranged in a checkerboard pattern. The probe light provided by the scanner system then comprises a pattern consisting of dark sections and sections with light having the same wavelength distribution as the multichromatic light source.

In order to obtain a digital 3D representation expressing both surface geometry and color representation of an object, i.e. a colored digital 3D representation of said part of the object surface, typically several sub-scans, i.e. partial representations of the object, have to be combined, where each sub-scans presents one view of the object. A sub-scan expressing a view from a given relative position preferably records the geometry and color of the object surface as seen from that relative position.

For a focus scanner, a view corresponds to one pass of the focusing element(s), i.e. for a focus scanner each sub-scan is the surface geometry and color derived from the stack of 2D images recorded during the pass of the focus plane position between its extremum positions.

The surface geometry found for various views can be combined by algorithms for stitching and registration as widely known in the literature, or from known view positions and orientations, for example when the scanner is mounted on axes with encoders. Color can be interpolated and averaged by methods such as texture weaving, or by simply averaging corresponding color components in multiple views of the same location on the surface. Here, it can be advantageous to account for differences in apparent color due to different angles of incidence and reflection, which is possible because the surface geometry is also known. Texture weaving is described by e.g. Callieri M, Cignoni P, Scopigno R. "Reconstructing textured meshes from multiple range rgb maps". VMV 2002, Erlangen, Nov. 20-22, 2002.

In some embodiments, the scanner and/or the scanner system is configured for generating a sub-scan of the object surface based on the obtained surface color and surface geometry. In some embodiments, the scanner and/or the scanner system is configured for combining sub-scans of the object surface obtained from different relative positions to generate a digital 3D representation expressing the surface geometry and color of at least part of the object.

In some embodiments, the combination of sub-scans of the object to obtain the digital 3D representation expressing surface geometry and color comprises computing the color in each surface point as a weighted average of corresponding points in all overlapping sub-scans at that surface point. The weight of each sub-scan in the sum may be determined by several factors, such as the presence of saturated pixel values or the orientation of the object surface with respect to the scanner when the sub-scan is recorded.

Such a weighted average is advantageous in cases where some scanner positions and orientations relative to the object will give a better estimate of the actual color than other positions and orientations. If the illumination of the object surface is uneven this can to some degree also be compensated for by weighting the best illuminated parts higher.

In some embodiments, the data processing system of the scanner system comprises an image processor configured for performing a post-processing of the surface geometry, the surface color readings, or the derived sub-scan or the digital 3D representation of the object. The scanner system may be configured for performing the combination of the sub-scans using e.g. computer implemented algorithms executed by the image processor.

The scanner system may be configured for performing the combination of the sub-scans using e.g. computer implemented algorithms executed by the data processing system as part of the post-processing of the surface geometry, surface color, sub-scan and/or the digital 3D representation, i.e. the post-processing comprises computing the color in each surface point as a weighted average of corresponding points in all overlapping sub-scans at that surface point.

Saturated pixel values should preferably have a low weight to reduce the effect of highlights on the recording of the surface color. The color for a given part of the surface should preferably be determined primarily from 2D images where the color can be determined precisely which is not the case when the pixel values are saturated.

In some embodiments, the scanner and/or scanner system is configured for detecting saturated pixels in the captured 2D images and for mitigating or removing the error in the obtained color caused by the pixel saturation. The error caused by the saturated pixel may be mitigated or removed by assigning a low weight to the saturated pixel in the weighted average.

Specularly reflected light has the color of the light source rather than the color of the object surface. If the object surface is not a pure white reflector then specular reflections can hence be identified as the areas where the pixel color closely matches the light source color. When obtaining the surface color it is therefore advantageous to assign a low weight to pixels or pixel groups whose color values closely match the color of the multichromatic light source in order to compensate for such specular reflections.

Specular reflections may also be a problem when intra orally scanning a patient's set of teeth since teeth rarely are completely white. It may hence be advantageous to assume that for pixels where the readings from the color images sensor indicate that the surface of the object is a pure white reflector, the light recorded by this pixel group is caused by a specular reflection from the teeth or the soft tissue in the oral cavity and accordingly assign a low weight to these pixels to compensate for the specular reflections.

In some embodiments, the compensation for specular reflections from the object surface is based on information derived from a calibration of the scanner in which a calibration object e.g. in the form of a pure white reflector is scanned. The color image sensor readings then depend on the spectrum of the multichromatic light source and on the wavelength dependence of the scanner's optical system caused by e.g. a wavelength dependent reflectance of mirrors in the optical system. If the optical system guides light equally well for all wavelengths of the multichromatic light source, the color image sensor will record the color (also referred to as the spectrum) of the multichromatic light source when the pure white reflector is scanned.

In some embodiments, compensating for the specular reflections from the surface is based on information derived from a calculation based on the wavelength dependence of the scanner's optical system, the spectrum of the multichromatic light source and a wavelength dependent sensitivity of the color image sensor. In some embodiments, the scanner comprises means for optically suppressing specularly reflected light to achieve better color measurement. This may be provided if the scanner further comprises means for polarizing the probe light, for example by means of at least one polarizing beam splitter. When scanning inside an oral cavity there may be red ambient light caused by probe light illumination of surrounding tissue, such as the gingiva, palette, tongue or buccal tissue. In some embodiments, the scanner and/or scanner system is hence configured for suppressing the red component in the recorded 2D images.

In some embodiments, the scanner and/or scanner system is configured for comparing the color of sections of the captured 2D images and/or of the sub-scans of the object with predetermined color ranges for teeth and for oral tissue, respectively, and for suppressing the red component of the recorded color for sections where the color is not in either one of the two predetermined color ranges. The teeth may e.g. be assumed to be primarily white with one ratio between the intensity of the different components of the recorded image, e.g. with one ratio between the intensity of the red component and the intensity of the blue and/or green components in a RGB configuration, while oral tissue is primarily reddish with another ratio between the intensity of the components. When a color recorded for a region of the oral cavity shows a ratio which differs from both the predetermined ratio for teeth and the predetermined ratio for tissue, this region is identified as a tooth region illuminated by red ambient light and the red component of the recorded image is suppressed relative to the other components, either by reducing the recorded intensity of the red signal or by increasing the recorded intensities of the other components in the image.

In some embodiments, the color of points with a surface normal directly towards the scanner are weighted higher than the color of points where the surface normal is not directed towards the scanner. This has the advantage that points with a surface normal directly towards the scanner will to a higher degree be illuminated by the white light from the scanner and not by the ambient light.

In some embodiments, the color of points with a surface normal directly towards the scanner are weighted lower if associated with specular reflections.

In some embodiments the scanner is configured for simultaneously compensating for different effects, such as compensating for saturated pixels and/or for specular reflections and/or for orientation of the surface normal. This may be done by generally raising the weight for a selection of pixels or pixel groups of a 2D image and by reducing the weight for a fraction of the pixels or pixel groups of said selection.

In some embodiments, the method comprises a processing of recorded 2D images, a sub-scan or the generated 3D representations of the part of the object, where said processing comprises
  compensating for pixel saturation by omitting or reducing the weight of saturated pixels when deriving the surface color, and/or
  compensating for specular reflections when deriving the surface color by omitting or reducing the weight of pixels whose color values closely matches the light source color, and/or
  compensating for red ambient light by comparing surface color information of the 2D images with predetermined color ranges, and suppressing the red component of the recorded color if this is not within a predetermined color range.

Disclosed is a method of using the disclosed scanner system to display color texture on the generated digital 3D representation of the object. It is advantageous to display the color data as a texture on the digital 3D representation, for example on a computer screen. The combination of color and geometry is a more powerful conveyor of information than either type of data alone. For example, dentists can more easily differentiate between different types of tissue. In the rendering of the surface geometry, appropriate shading can help convey the surface geometry on the texture, for example with artificial shadows revealing sharp edges better than texture alone could do.

When the multichromatic light source is a multi-die LED or similar, the scanner system can also be used to detect fluorescence. Disclosed is a method of using the disclosed scanner system to display fluorescence on surface geometry.

In some embodiments, the scanner is configured for exciting fluorescence on said object by illuminating it with only a subset of the LED dies in the multi-die LED, and where said fluorescence is recorded by only or preferentially reading out only those pixels in the color image sensor that have color filters at least approximately matching the color of the fluoresced light, i.e. measuring intensity only in pixels of the image sensors that have filters for longer-wavelength light. In other words, the scanner is capable of selectively activating only a subset of the LED dies in the multi-die LED and of only recording or preferentially reading out only those pixels in the color image sensor that have color filters at a higher wavelength than that of the subset of the LED dies, such that light emitted from the subset of LED dies can excite fluorescent materials in the object and the scanner can record the fluorescence emitted from these fluorescent materials. The subset of the dies preferably comprises one or more LED dies which emits light within the excitation spectrum of the fluorescent materials in the object, such as an ultraviolet, a blue, a green, a yellow or a red LED die. Such fluorescence measurement yields a 2D data array much like the 2D color image, however unlike the 2D image it cannot be taken concurrently with the surface geometry. For a slow-moving scanner, and/or with appropriate interpolation, the fluorescence image can still be overlaid the surface geometry. It is advantageous to display fluorescence on teeth because it can help detect caries and plaque.

In some embodiments, the data processing system comprises a microprocessor unit configured for extracting the surface geometry information from 2D images obtained by the color image sensor and for determining the surface color from the same images.

The data processing system may comprise units distributed in different parts of the scanner system. For a scanner system comprising a handheld part connected to a stationary unit, the data processing system may for example comprise one unit integrated in the handheld part and another unit integrated in the stationary unit. This can be advantageous when a data connection for transferring data from the handheld unit to the stationary unit has a bandwidth which cannot handle the data stream from the color image sensor. A preliminary data processing in the handheld unit can then reduce the amount of data which must be transferred via the data connection.

In some embodiments, the data processing system comprises a computer readable medium on which is stored computer implemented algorithms for performing said post-processing.

In some embodiments, a part of the data processing system is integrated in a cart or a personal computer.

Disclosed is a method of using the disclosed scanner system to average color and/or surface geometry from several views, where each view represents a substantially fixed relative orientation of scanner and object.

Disclosed is a method using the disclosed scanner system to combine color and/or surface geometry from several views, where each view represents a substantially fixed relative orientation of scanner and object, such as to achieve a more complete coverage of the object than would be possible in a single view.

Disclosed is a scanner for obtaining surface geometry and surface color of an object, the scanner comprising:
  a multichromatic light source configured for providing a probe light, and
  a color image sensor comprising an array of image sensor pixels for recording one or more 2D images of light received from said object,
where at least for a block of said image sensor pixels, both surface color and surface geometry of a part of the object are derived at least partly from one 2D image recorded by said color image sensor Disclosed is a scanner system for recording surface geometry and surface color of an object, the scanner system comprising:
  a multichromatic light source configured for providing a multichromatic probe light, and
  a color image sensor comprising an array of image sensor pixels for capturing one or more 2D images of light received from said object, where at least for a block of said image sensor pixels, both surface color information and surface geometry information of a part of the object are derived at least partly from one 2D image captured by said color image sensor.

Disclosed is a scanner system for recording surface geometry and surface color of an object, the scanner system comprising:
a multichromatic light source configured for providing a probe light,
a color image sensor comprising an array of image sensor pixels, and
an optical system configured for guiding light received from the object to the color image sensor such that 2D images of said object can be captured by said color image sensor;
wherein the scanner system is configured for capturing a number of said 2D images of a part of the object and for deriving both surface color information and surface geometry information of the part of the object from at least one of said captured 2D images at least for a block of said color image sensor pixels, such that the surface color information and the surface geometry information are obtained concurrently by the scanner.

Disclosed is a scanner system for recording surface geometry and surface color of an object, the scanner system comprising:
a multichromatic light source configured for providing a probe light;
a color image sensor comprising an array of image sensor pixels, where the image sensor is arranged to capture 2D images of light received from the object; and
an image processor configured for deriving both surface color information and surface geometry information of at least a part of the object from at least one of said 2D images captured by the color image sensor.

Disclosed is a scanner system for recording surface geometry and surface color of an object, said scanner system comprising
a scanner system according to any of the embodiments, where the scanner system is configured for deriving surface color and surface geometry of the object, and optionally for generating a sub-scan or a digital 3D representation of the part of the object; and
a data processing unit configured for post-processing surface geometry and/or surface color readings from the color image sensor, or for post-processing the generated sub-scan or digital 3D representation.

Disclosed is a method of recording surface geometry and surface color of an object, the method comprising:
providing a scanner or scanner system according to any of the embodiments;
illuminating the surface of said object with probe light from said multichromatic light source;
recording one or more 2D images of said object using said color image sensor; and
deriving both surface color and surface geometry of a part of the object from at least some of said recorded 2D images at least for a block of said image sensor pixels, such that the surface color and surface geometry are obtained concurrently by the scanner.

BRIEF DESCRIPTION OF DRAWINGS

FIG. 1 shows a handheld part of a scanner system with components inside a housing 100. The scanner comprises a tip which can be entered into a cavity, a multichromatic light source in the form of a multi-die LED 101, pattern generating element 130 for incorporating a spatial pattern in the probe light, a beam splitter 140, color image sensor 180 including an image sensor 181, electronics and potentially other elements, an optical system typically comprising at least one lens, and the image sensor. The light from the light source 101 travels back and forth through the optical system 150. During this passage the optical system images the pattern 130 onto the object being scanned 200 which here is a patient's set of teeth, and further images the object being scanned onto the image sensor 181.

Figure 1:
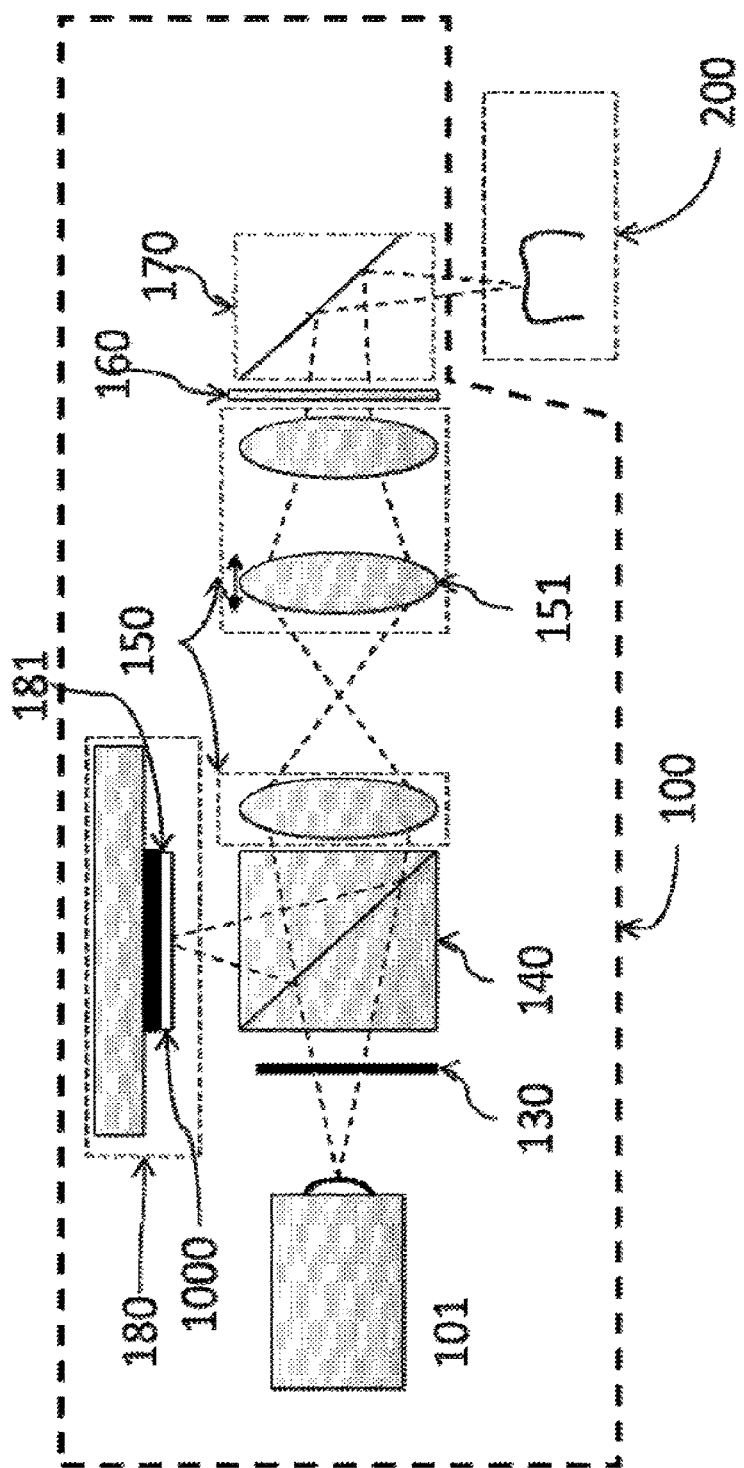
FIG. 1 shows a handheld embodiment of a scanner system.

The image sensor 181 has a color filter array 1000. Although drawn as a separate entity, the color filter array is typically integrated with the image sensor, with a single-color filter for every pixel.

The lens system includes a focusing element 151 which can be adjusted to shift the focal imaging plane of the pattern on the probed object 200. In the example embodiment, a single lens element is shifted physically back and forth along the optical axis.

As a whole, the optical system provides an imaging of the pattern onto the object being probed and from the object being probed to the camera.

The device may include polarization optics 160. Polarization optics can be used to selectively image specular reflections and block out undesired diffuse signal from sub-surface scattering inside the scanned object. The beam splitter 140 may also have polarization filtering properties. It can be advantageous for optical elements to be anti-reflection coated.

The device may include folding optics, a mirror 170, which directs the light out of the device in a direction different to the optical path of the lens system, e.g. in a direction perpendicular to the optical path of the lens system.

There may be additional optical elements in the scanner, for example one or more condenser lens in front of the light source 101.

In the example embodiment, the LED 101 is a multi-die LED with two green, one red, and one blue die. Only the green portion of the light is used for obtaining the surface geometry. Accordingly, the mirror 170 is coated such as to optimize preservation of the circular polarization of the green light, and not that of the other colors. Note that during scanning all dies within the LED are active, i.e., emitting light, so the scanner emits apparently white light onto the scanned object 200. The LED may emit light at the different colors with different intensities such that e.g. one color is more intense than the other colors. This may be desired in order to reduce cross-talk between the readings of the different color signals in the color image sensor. In case that the intensity of e.g. the red and blue diodes in a RGB system is reduced, the apparently white light emitted by the light source will appear greenish-white.

The scanner system further comprises a data processing system configured for deriving both surface geometry information and surface color information for a block of pixels of the color image sensor 180 at least partly from one 2D image recorded by said color image sensor 180. At least part of the data processing system may be arranged in the illustrated handheld part of the scanner system. A part may also be arranged in an additional part of the scanner system, such as a cart connected to the handheld part.

Figures 2A, 2B, 3A, 3B, 4:
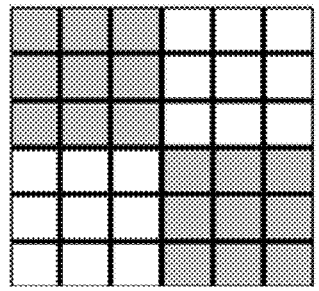
FIGS. 2A-2B show prior art pattern generating means and associated reference weights.
FIGS. 3A-3B show a pattern generating means and associated reference weights.
FIG. 4 shows a color filter array.

FIGS. 2A-2B show a section of a prior art pattern generating element 130 that is applied as a static pattern in a spatial correlation embodiment of WO2010145669, as imaged on a monochromatic image sensor 180. The pattern can be a chrome-on-glass pattern. The section shows only a portion of the pattern is shown, namely one period. This period is represented by a pixel block of 6 by 6 image pixels, and 2 by 2 pattern fields. The fields drawn in gray in FIG. 2A are in actuality black because the pattern mask is opaque for these fields; gray was only chosen for visibility and thus clarity of the Figure. FIG. 2B illustrates the reference weights f for computing the spatial correlation measure A for the pixel block, where n=6×6=36, such that $$A = \sum_{i=1}^{n} f_i I_i$$

where I are the intensity values measured in the 36 pixels in the pixel block for a given image. Note that perfect alignment between image sensor pixels and pattern fields is not required, but gives the best signal for the surface geometry measurement.

FIGS. 3A-3B show the extension of the principle in FIGS. 2A-2B to color scanning. The pattern is the same as in FIGS. 2A-2B and so is the image sensor geometry. However, the image sensor is a color image sensor with a Bayer color filter array. In FIG. 3A, pixels marked "B" have a blue color filter, while "G" indicates green and "R" red pixel filters, respectively. FIG. 3B shows the corresponding reference weights f. Note that only green pixels have a non-zero value. This is so because only the green fraction of the spectrum is used for recording the surface geometry information.

For the pattern/color filter combination of FIGS. 3A-3B, a color component $c_j$ within a pixel block can be obtained as $$c_j = \sum_{i=1}^{n} g_{j,i} I_i$$

where $g_{j,i}=1$ if pixel i has a filter for color $c_j$, 0 otherwise. For an RGB color filter array like in the Bayer pattern, j is one of red, green, or blue. Further weighting of the individual color components, i.e., color calibration, may be required to obtain natural color data, typically as compensation for varying filter efficiency, illumination source efficiency, and different fraction of color components in the filter pattern. The calibration may also depend on focus plane location and/or position within the field of view, as the mixing of the LED's component colors may vary with those factors.

FIG. 4 shows an inventive color filter array with a higher fraction of green pixels than in the Bayer pattern. The color filter array comprises a plurality of cells of 6×6 color filters, with blue color filters in positions (2,2) and (5,5) of each cell, red color filters in positions (2,5) and (5,2), a and green color filters in all remaining positions of the cell.

Assuming that only the green portion of the illumination is used to obtain the surface geometry information, the filter of FIG. 4 will potentially provide a better quality of the obtained surface geometry than a Bayer pattern filter, at the expense of poorer color representation. The poorer color representation will however in many cases still be sufficient while the improved quality of the obtained surface geometry often is very advantageous.

Figure 5:
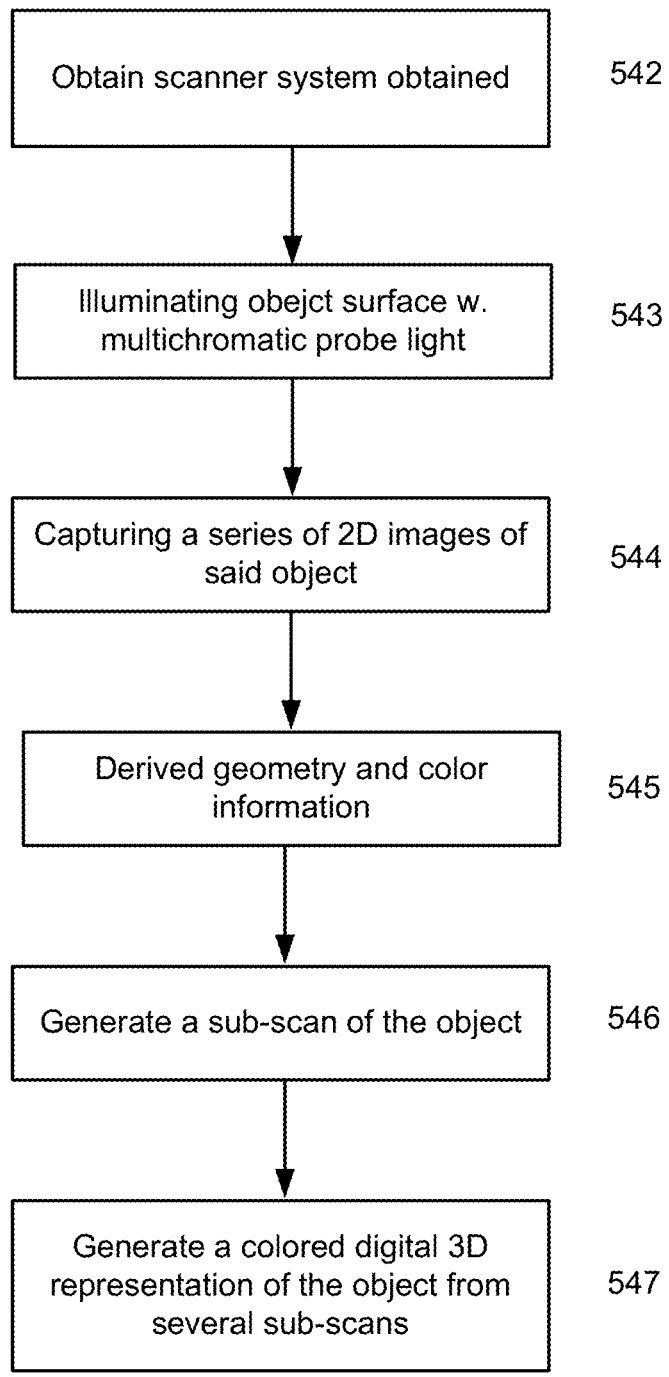
FIG. 5 shows a flow chart of a method.

FIG. 5 illustrates a flow chart 541 of a method of recording surface geometry and surface color of an object.

In step 542 a scanner system according to any of the previous claims is obtained.

In step 543 the object is illuminated with multichromatic probe light. In a focus scanning system utilizing a correlation measure or correlation measure function, a checkerboard pattern may be imposed on the probe light such that information relating to the pattern can be used for determining surface geometry information from captured 2D images.

In step 544 a series of 2D images of said object is captured using said color image sensor. The 2D images can be processed immediately or stored for later processing in a memory unit.

In step 545 both surface geometry information and surface color information are derived for a block of image sensor pixels at least partly from one captured 2D image. The information can e.g. be derived using the correlation measure approach as descried herein.

The derived informations are combined to generate a sub-scan of the object in step 546, where the sub-scan comprises data expressing the geometry and color of the object as seen from one view.

In step 547 a digital 3D representation expressing both color and geometry of the object is generated by combining several sub-scans. This may be done using known algorithms for sub-scan alignment such as algorithms for stitching and registration as widely known in the literature.

Figure 6A:
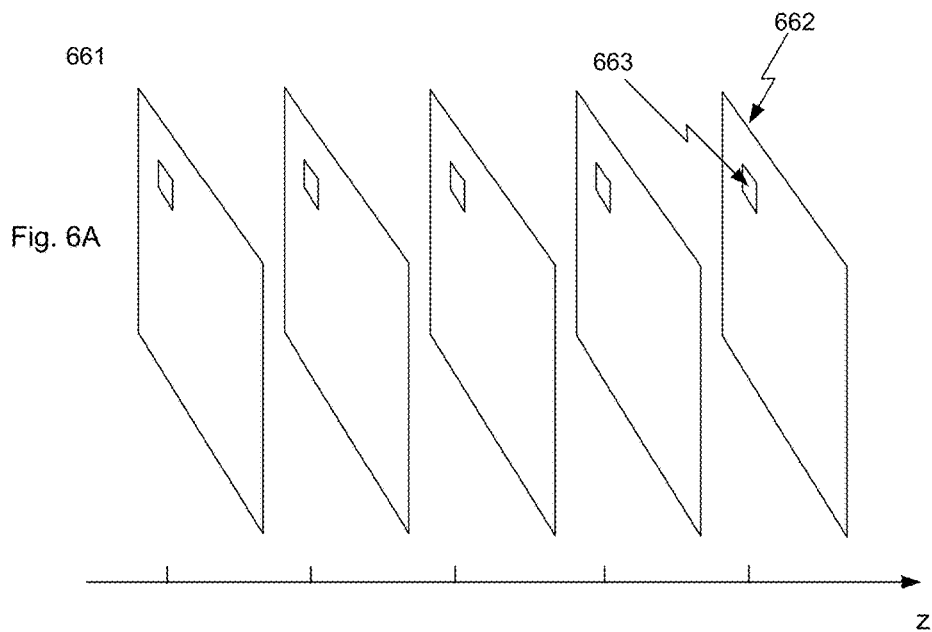
FIGS. 6A-6C illustrate how surface geometry information and surface geometry information can be derived.
Figure 6B:
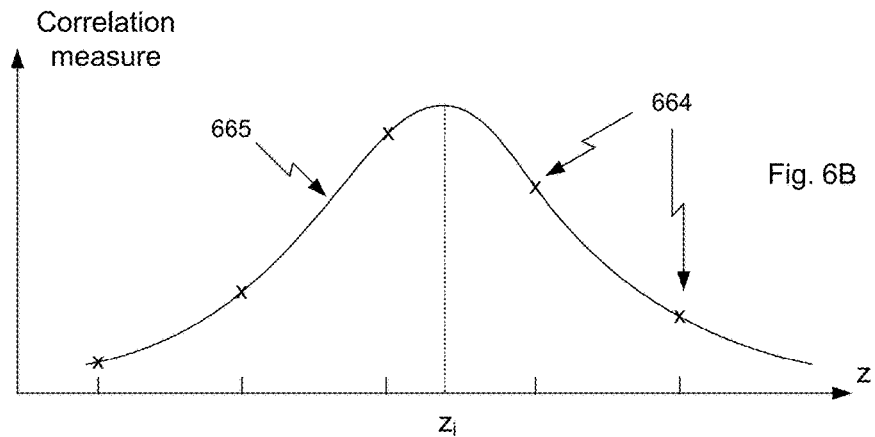
Figure 6C:
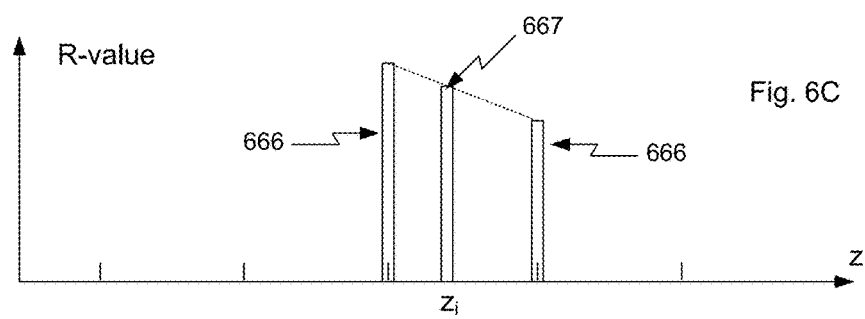

FIGS. 6A-C illustrate how surface geometry information and surface geometry information can be derived at least from one 2D image for a block of image sensor pixels.

The correlation measure is determined for all active image sensor pixel groups on the color image sensor for every focus plane position, i.e. for every 2D image of the stack. Starting by analyzing the 2D images from one end of the stack, the correlation measures for all active image sensor pixel groups is determined and the calculated values are stored. Progressing through the stack the correlation measures for each pixel group are determined and stored together with the previously stored values, i.e. the values for the previously analyzed 2D images.

A correlation measure function describing the variation of the correlation measure along the optical axis is then determined for each pixel group by smoothing and interpolating the determined correlation measure values. For example, a polynomial can be fitted to the values of for a pixel block over several images on both sides of the recorded maximum, and a location of a deducted maximum can be found from the maximum of the fitted polynomial, which can be in between two images.

The surface color information for the pixel group is derived from one or more of the 2D images from which the position of the correlation measure maximum was determined i.e. surface geometry information and surface color information from a group of pixels of the color image sensor are derived from the same 2D images of the stack.

The surface color information can be derived from one 2D image. The maximum value of the correlation measure for each group of pixels is monitored along the analysis of the 2D images such that when a 2D image has been analyzed the values for the correlation measure for the different pixels groups can be compared with the currently highest value for the previously analyzed 2D images. If the correlation measure is a new maximum value for that pixel group at least the portion of the 2D image corresponding to this pixel group is saved. Next time a higher correlation value is found for that pixel group the portion of this 2D image is saved overwriting the previously stored image/sub-image. Thereby when all 2D images of the stack have been analyzed, the surface geometry information of the 2D images is translated into a series of correlation measure values for each pixel group where a maximum value is recorded for each block of image sensor pixels.

FIG. 6A illustrated a portion 661 of a stack of 2D images acquired using a focus scanning system, where each 2D image is acquired at a different focal plane position. In each 2D image 662 a portion 663 corresponding to a block of image sensor pixels are indicated. The block corresponding to a set of coordinates $(x_i, y_i)$. The focus scanning system is configured for determining a correlation measure for each block of image sensor pixels and for each 2D image in the stack. In FIG. 6B is illustrated the determined correlation measures 664 (here indicated by an "x") for the block 663. Based on the determined correlation measures 664 a correlation measure function 665 is calculated, here as a polynomial, and a maximum value for the correlation measure function is found a position $z_i$. The z-value for which the fitted polynomial has a maximum $(z_i)$ is identified as a point of the object surface. The surface geometry information derived for this block can then be presented in the form of the coordinates $(x_i, y_i, z_i)$, and by combining the surface geometry information for several block of the images sensor, the a sub-scan expressing the geometry of part of the object can be created.

In FIG. 6C is illustrated a procedure for deriving the surface color geometry from two 2D images for each block of image sensor pixels. Two 2D images are stored using the procedure described above and their RGB values for the pixel block are determined. In FIG. 6C the R-values 666 are displayed. An averaged R-value 667 (as well as averaged G- and B-values) at the $z_i$ position can then be determined by interpolation and used as surface color information for this block. This surface colir information is evidently derived from the same 2D image that the geometry information at least in part was derived from.

The invention claimed is:
1. A scanner system for recording surface geometry and surface color of an object, the scanner system comprising:
 a multichromatic light source configured to provide a multichromatic probe light for illumination of the object,
 a color image sensor comprising an array of image sensor pixels to capture one or more 2D images of light received from the object, the color image sensor comprising a color filter array, and
 a data processing system configured to derive surface geometry information for a first set of image pixels within a block of the image sensor pixels from a series of 2D images recorded by the color image sensor,
 the data processing system further configured to derive surface color information for a second set of image pixels within the block of the image sensor pixels from at least one 2D image recorded by the color image sensor, wherein the surface color information is obtained by demosaicing the second set of the image sensor pixels,
 wherein the first set of the image sensor pixels is different from the second set of the image sensor pixels.
2. The scanner system according to claim 1, wherein the first set of the image sensor pixels and the second set of the image sensor pixels are based on differently weighing the image sensor pixels within the image block.
3. The scanner system according to claim 1, wherein the first set of the image sensor pixels is larger than the second set of the image sensor pixels.
4. The scanner system according to claim 1, wherein the first set of the image sensor pixels is smaller than the second set of the image sensor pixels.
5. The scanner system according to claim 1, wherein the second set of the image sensor pixels comprises a part of the first set of the image sensor pixels.
6. The scanner system according to claim 1, wherein the first set of the image sensor pixels comprises a part of the second set of the image sensor pixels.
7. The scanner system according to claim 1, wherein the first set of the image sensor pixels comprises a part that is excluded from the second set of the image sensor pixels.
8. The scanner system according to claim 1, wherein the color filter array is a Bayer filter array.
9. The scanner system according to claim 1, wherein the data processing system is configured to generate a sub-scan of a part of the object surface based on surface geometry information and surface color information derived from a plurality of blocks of image sensor pixels which include the block of the image sensor pixels.
10. The scanner system according to claim 1, wherein the scanner system comprises a pattern generating element configured to incorporate a spatial pattern in the probe light.
11. The scanner system according to claim 10, wherein the pattern generating element is configured to provide that the spatial pattern comprises alternating dark and bright regions arranged in a checkerboard pattern.
12. The scanner system according to claim 1, wherein the data processing system is configured to derive the surface geometry information by calculating for several 2D images of the series of 2D images a correlation measure between a portion of the at least one 2D image recorded by the block of the image sensor pixels and a weight function, wherein the weight function is determined based on information of the configuration of the spatial pattern.
13. The scanner system according to claim 12, wherein the data processing system is configured to derive the surface geometry information for the block of the image sensor pixels by identifying the position along an optical axis of the scanner system at which the corresponding correlation measure has a maximum value.
14. The scanner system according to claim 9, wherein the data processing system is configured to generate the sub-scan by determining a correlation measure function describing the variation of the correlation measure along the optical axis for each of the plurality of blocks of the image sensor pixels, and identifying the position along the optical axis at which the correlation measure functions have their maximum value for the block.
15. The scanner system according to claim 14, wherein the maximum value of the correlation measure is the highest calculated value of the correlation measure for the block of the image sensor pixels and/or the highest maximum value of the correlation measure function for the block of the image sensor pixels.
16. The scanner system according to claim 13, wherein the data processing system is configured to determine a sub-scan color for a point on a generated sub-scan based on the surface color information of one of the 2D images of the series of 2D images in which the correlation measure has its maximum value for the corresponding block of the image sensor pixels.

17. The scanner system according to claim 16, wherein the data processing system is configured to derive the sub-scan color for a point on a generated sub-scan based on the surface color information of 2D images in the series of 2D images in which the correlation measure has its maximum value for the corresponding block of the image sensor pixels and on at least one additional 2D image.

18. The scanner system according to claim 17, wherein the at least one additional 2D image comprises a neighboring 2D image from the series of 2D images.

19. The scanner system according to claim 17, wherein the data processing system is configured to interpolate surface color information of at least two 2D images in a series when determining the sub-scan color.

20. The scanner system according to claim 19, wherein the interpolation is of surface color information of neighboring 2D images in a series.

21. The scanner system according to claim 17, wherein the data processing system is configured to compute an averaged sub-scan color for a number of points of the sub-scan, wherein the computing comprises an averaging of sub-scan colors of different points.

22. The scanner system according to claim 21, wherein the averaging of sub-scan colors of different points comprises a weighted averaging of the colors of the surrounding points on the sub-scan.

23. The scanner system according to claim 1, wherein the data processing system is configured to:
detect a saturated pixel in 2D images recorded by the block of the image sensor pixels; and
mitigate or remove the error in the derived surface color information or the sub-scan color caused by the saturated pixel.

24. The scanner system according to claim 23, wherein the error caused by the saturated pixel is mitigated or removed by assigning a low weight to the surface color information of the saturated pixel in the computing of the smoothed sub-scan color and/or by assigning a low weight to the sub-scan color computed based on the saturated pixel.

25. The scanner system according to claim 1, wherein the data processing system is configured to:
compare the derived surface color information of sections of 2D images recorded by a plurality of blocks of the image sensor pixels or of the generated sub-scans of the object with predetermined color ranges for teeth and for oral tissue; and
suppress a red component of the derived surface color information or sub-scan color for sections wherein the derived surface color is not in one of the two predetermined color ranges.

26. The scanner system according to claim 1, wherein the color filter array comprises at least three types of color filters, each allowing light in a known wavelength range, W1, W2, and W3 respectively, to propagate through the color filter.

27. The scanner system according to claim 26, wherein the surface geometry information is derived from light in a selected wavelength range of the spectrum provided by the multichromatic light source.

28. The scanner system according to claim 27, wherein the color filter array is such that the proportion of the image sensor pixels of the color image sensor with color filters that match the selected wavelength range of the spectrum has a proportion that equals 32/36, 60/64 or 96/100.

29. The scanner system according to claim 27, wherein the color filter array is such that the proportion of the image sensor pixels of the color image sensor with color filters that match the selected wavelength range of the spectrum is larger than 50%.

30. The scanner system according to claim 27, wherein the selected wavelength range matches the W2 wavelength range.

31. The scanner system according to claim 26, wherein the color filter array comprises a plurality of cells of 6×6 color filters, wherein the color filters in positions (2,2) and (5,5) of each cell are of the W1 type, the color filters in positions (2,5) and (5,2) are of the W3 type.

32. The scanner system according to claim 31, wherein the remaining 32 color filters in the 6×6 cell are of the W2 type.

33. The scanner system according to claim 1, wherein the multichromatic light source, the color image sensor, and at least a portion of the data processing system are included in a hand held unit.

34. The scanner system according to claim 1, wherein the data processing system is further configured to:
combine a number of sub-scans to generate a digital 3D representation of the object; and
determine object color of a least one point of the generated digital 3D representation of the object from sub-scan color of the sub-scans combined to generate the digital 3D representation, such that the digital 3D representation expresses both geometry and color profile of the object,
wherein determining the object color comprises computing a weighted average of sub-scan color values derived for corresponding points in overlapping sub-scans at that point of the object surface.

35. The scanner system according to claim 1,
wherein the color image sensor comprises a color filter array comprising at least three types of colors filters, each allowing light in a known wavelength range, W1, W2, and W3 respectively, to propagate through the color filter,
wherein the data processing system is configured to:
derive surface color information for the block of the image sensor pixels from at least one of the one or more 2D images used to derive the surface geometry information; and
derive the surface geometry information is derived from light in a selected wavelength range of the spectrum provided by the multichromatic light source, and
wherein the color filter array is such that its proportion of pixels with color filters that match the selected wavelength range of the spectrum is larger than 50%.

36. The scanner system according to claim 1, wherein the data processing system is further configured to:
derive surface color information for the block of the image sensor pixels from at least one of the one or more 2D images used to derive the surface geometry information,
wherein the color filter array comprises at least three types of colors filters, each allowing light in a known wavelength range, W1, W2, and W3 respectively, to propagate through the color filter and the filters are arranged in a plurality of cells of 6×6 color filters, and
wherein the color filters in positions (2,2) and (5,5) of each cell are of the W1 type, and the color filters in positions (2,5) and (5,2) are of the W3 type.

37. The scanner system according to claim 36, wherein the remaining 32 color filters in the 6×6 cell are of the W2 type.

38. The scanner system according to claim 1, wherein the data processing system is further configured to:
- derive surface color information for the block of the image sensor pixels from at least one of the one or more 2D images used to derive the surface geometry information, wherein deriving the surface geometry information and surface color information comprises calculating, for several 2D images of the series of 2D images, a correlation measure between a portion of the at least one 2D image recorded by the block of the image sensor pixels and a weight function, wherein the weight function is determined based on information of the configuration of the spatial pattern;
- identify the position along the optical axis at which the corresponding correlation measure has a maximum value;
- determine a sub-scan color for a point on a generated sub-scan based on the surface color information of one of the 2D images of the series of 2D images in which the correlation measure has its maximum value for the corresponding block of the image sensor pixels; and
- compute an averaged sub-scan color for a number of points of the sub-scan, wherein the computing comprises an averaging of sub-scan colors of surrounding points on the sub-scan.

39. The scanner system according to claim 38, wherein the averaging of sub-scan colors of surrounding points comprises a weighted averaging of the colors of the surrounding points on the sub-scan.

40. The scanner system according to claim 1, wherein the scanner system is configured to operate by translating a focus plane along an optical axis of the scanner system to capture the one or more 2D images.

41. The scanner system according to claim 1, wherein the scanner system is based on triangularization.

42. The scanner system according to claim 1, wherein the surface geometry information for a given block of the image sensor pixels is derived by identifying at which distance from the scanner system the object surface is in focus for that block of the image sensor pixels.

43. The scanner system according to claim 1, wherein the scanner is configured to derive the surface color with a higher resolution than the surface geometry.

44. The scanner system according to claim 1, wherein the illumination source is defocused at the object plane to achieve uniform illumination.

45. The scanner system according to claim 1,
- wherein the scanner system comprises a handheld part and a stationary part, the handheld part being connected for data communication to the stationary part,
- wherein a portion of the data processing system is integrated in the handheld part,
- and wherein another portion of the data processing system is integrated in the stationary part.

46. The scanner system according to claim 45,
- wherein a portion of the data processing system integrated in the handheld part is configured to process the one or more 2D images recorded by the color image sensor.

47. The scanner system according to claim 1,
- wherein the scanner system comprises a handheld part and a stationary part, the handheld part being connected for data communication to the stationary part,
- and wherein the data processing system is fully integrated in the handheld part.

48. The scanner system according to claim 1,
- wherein the multichromatic light source is a multi-die LED comprising multiple dies,
- wherein the scanner system is configured to excite fluorescence on the object by illuminating the object with only a subset of the multiple dies, record fluorescence by reading out only pixels in the color image sensor that have color filters at least approximately matching a color of fluoresced light, by selectively activating only the subset of the multiple dies and reading out only pixels in the color image sensor that have color filters at a higher wavelength than that of the subset of the multiple dies, such that the subset of the multiple dies are configured to emit light to excite fluorescent materials of the object and the scanner is configured to record fluorescence emitted from the fluorescent materials of the object,
- wherein the subset of the multiple dies comprises one or more LED dies configured to emit light within an excitation spectrum of the fluorescent materials of the object,
- wherein the reading out of the pixels yields a 2D data array distinct from the one or more 2D images recorded by the color image sensor,
- and wherein the 2D data array is overlaid on the surface geometry information.

49. The scanner system according to claim 1, wherein the data processing system is further configured to:
- derive surface color information for the block of the image sensor pixels from at least one of the one or more 2D images used to derive the surface geometry information, wherein deriving the surface geometry information and surface color information comprises calculating, for several 2D images of the series of 2D images, a correlation measure between a portion of the at least one 2D image recorded by the block of the image sensor pixels and a weight function, wherein the weight function is determined based on information of the configuration of the spatial pattern;
- identify the position along the optical axis at which the corresponding correlation measure has a maximum value;
- determine a sub-scan color for a point on a generated sub-scan based on the surface color information of one of the 2D images of the series of 2D images in which the correlation measure has its maximum value for the corresponding block of the image sensor pixels; and
- compute an averaged sub-scan color for a number of points of the sub-scan, wherein the computing comprises an averaging of sub-scan colors of surrounding points on the sub-scan,
- wherein the averaging of sub-scan colors of surrounding points comprises a weighted averaging of the colors of the surrounding points on the sub-scan,
- wherein the multichromatic light source is a multi-die LED comprising multiple dies,
- wherein the scanner system is further configured to excite fluorescence on the object by illuminating the object with only a subset of the multiple dies, record fluorescence by reading out only pixels in the color image sensor that have color filters at least approximately matching a color of fluoresced light, by selectively activating only the subset of the multiple dies and reading out only pixels in the color image sensor that have color filters at a higher wavelength than that of the subset of the multiple dies, such that the subset of the multiple dies are configured to emit light to excite fluorescent materials of the object and the scanner is configured to record fluorescence emitted from the fluorescent materials of the object, and wherein the subset of the multiple dies comprises one or more LED dies configured to emit light within an excitation spectrum of the fluorescent materials of the object.

50. The scanner system according to claim 1, wherein the scanner system comprises a handheld part which includes an elongated tip configured for intraoral access, and a folding device at the elongated tip configured to direct light emerging from the scanner system toward the object.

51. A method of recording surface geometry and surface color of an object, the method comprising:
obtaining a scanner system according to claim 1;
illuminating the surface of the object with multichromatic probe light from the multichromatic light source;
capturing a series of 2D images of the object using the color image sensor; and
deriving both surface geometry information and surface color information for a block of the image sensor pixels at least partly from one captured 2D image.

* * * * *